US012642483B2

(12) United States Patent
Gienger, IV et al.

(10) Patent No.: US 12,642,483 B2
(45) Date of Patent: Jun. 2, 2026

(54) BLUNT FORCE SENSOR ARRAY

(71) Applicant: The Johns Hopkins University,
Baltimore, MD (US)

(72) Inventors: Edwin B. Gienger, IV, Washington,
DC (US); John B. Helder, Columbia,
MD (US); Morgana M. Trexler,
Baltimore, MD (US); **Catherine M.
Carneal**, Silver Spring, MD (US);
Christopher J. Dohopolski, Baltimore,
MD (US); James C. Gurganus,
Aberdeen Proving Ground, MD (US);
William H. Mermagen, Aberdeen
Proving Ground, MD (US); **Michael S.
Horsmon**, Gunpowder, MD (US)

(73) Assignee: The Johns Hopkins University,
Baltimore, MD (US)

( * ) Notice: Subject to any disclaimer, the term of this
patent is extended or adjusted under 35
U.S.C. 154(b) by 837 days.

(21) Appl. No.: 17/588,538

(22) Filed: Jan. 31, 2022

(65) Prior Publication Data

US 2023/0147160 A1 May 11, 2023

Related U.S. Application Data

(60) Provisional application No. 63/168,503, filed on Mar.
31, 2021.

(51) Int. Cl.
*A61B 5/11* (2006.01)
*A61B 5/00* (2006.01)
*G01M 7/08* (2006.01)
(52) U.S. Cl.
CPC .... *A61B 5/4504* (2013.01); *A61B 2562/0219*
(2013.01); *A61B 2562/0261* (2013.01); *A61B
2562/164* (2013.01); *A61B 2562/18* (2013.01)

(58) Field of Classification Search
CPC .... A61B 5/45–4528; A61B 2562/0219; A61B
2562/0242–0266; A61B 2562/164;
(Continued)

(56) References Cited

U.S. PATENT DOCUMENTS

2016/0100794 A1* 4/2016 Miller .................. A61B 5/0036
607/110
2020/0022601 A1* 1/2020 Rogers ..................... A61B 5/29
(Continued)

OTHER PUBLICATIONS

Hoshaw, S.J et al. "A Method Suitable for in Vivo Measurement of
Bone Strain in Humans." Journal of biomechanics 30.5 (1997):
521-524. Web. (Year: 1997).*
(Continued)

*Primary Examiner* — Matthew Kremer
*Assistant Examiner* — Aaron Merriam
(74) *Attorney, Agent, or Firm* — Noah J. Hayward

(57) ABSTRACT

A blunt force sensor array for application to a non-planar
surface includes a flexible thin-film substrate, a plurality of
force sensors secured to the flexible thin-film substrate
proximate to a center measurement point, a strain gauge
secured on the flexible thin-film substrate proximate to the
center measurement point, and a sensor interface configured
to connect to external measurement and control circuitry.
The sensor interface may be electrically connected to each
of the force sensors and the strain gauge via traces disposed
on the flexible thin-film substrate. The flexibility and shape
of the flexible thin-film substrate may permit the blunt force
sensor array to be applied to the non-planar surface to detect
forces and strains experienced by the non-planar surface in
response to a blunt force event on the non-planar surface.

20 Claims, 5 Drawing Sheets

(58) Field of Classification Search
CPC ..... A61B 2562/18; A61B 5/11; A61B 5/1036;
A61B 5/6861; A61B 5/6878; G01L
5/0028–0052; G01M 7/08
See application file for complete search history.

(56) References Cited

U.S. PATENT DOCUMENTS

2020/0049580 A1* 2/2020 Yin ....................... G01L 1/2287
2021/0378574 A1* 12/2021 Sabesan ................. A61B 5/291

OTHER PUBLICATIONS

Tekscan, Inc., "K-Scan System," product disclosure, Tekscan, Inc.,
Norwood, MA, available at web.archive.org/web/20191014034618/
www.tekscan.com/products-solutions/systems/k-scan-system, 2019,
accessed Mar. 13, 2026 (Year: 2019).*

* cited by examiner

BLUNT FORCE SENSOR ARRAY

CROSS-REFERENCE TO RELATED APPLICATIONS

This application claims priority to and the benefit of prior-filed, co-pending U.S. Provisional Application No. 63/168,503 filed on Mar. 31, 2021, the entire contents of which are hereby incorporated herein by reference.

STATEMENT OF GOVERNMENTAL INTEREST

This invention was made with Government support under contract number N00024-13-D-6400 awarded by the Naval Sea Systems Command (NAVSEA). The Government has certain rights in the invention.

TECHNICAL FIELD

Example embodiments generally relate to sensor technologies, and in particular force sensor technologies including pressure and strain forces.

BACKGROUND

Sensor technologies have become ubiquitous for use in a variety of testing environments, as well as, in completed products. For example, automobiles utilize impact sensors to detect a collision to trigger the deployment of an air bag. Such force sensors are not space-constrained and can therefore be placed within the body of the vehicle with relative ease. However, in many implementations, particularly in test environments, space and other limitations can exist. Additionally, the presence of testing sensors should not change the results of the test. As such, an ideal test sensor is one that is present within the test environment to take the necessary measurements, but otherwise takes up no space and its presence has no impact on the measurements.

An example testing environment where strict requirements on sensors exist is in the helmet testing and development space, and, in particular, with respect to testing that is performed to measure behind helmet blunt trauma (BHBT). In this regard, sensors are needed that can measure the forces transferred to, for example, the skull by the interior of a helmet in response to an impact on the helmet. Conventional sensors that could be used for such testing are too large to be able to perform a proper test. Therefore, there is a need for an improved sensor that can be utilized in space-constrained testing environments without having a significant effect on the forces that are to be measured.

BRIEF SUMMARY

According to some example embodiments, a blunt force sensor array for application to a non-planar surface is provided. The blunt force sensor array may include, i.e. comprise, a flexible thin-film substrate, a plurality of force sensors secured to the flexible thin-film substrate proximate to a center measurement point, a strain gauge secured on the flexible thin-film substrate proximate to the center measurement point, and a sensor interface configured to connect to external measurement and control circuitry. In this regard, the sensor interface may be electrically connected to each of the force sensors and the strain gauge via traces disposed on the flexible thin-film substrate. A flexibility and a shape of the flexible thin-film substrate may permit the blunt force sensor array to be applied to the non-planar surface to detect forces and strains experienced by the non-planar surface in response to a blunt force event on the non-planar surface.

According to some example embodiments, a blunt force measurement system is provided. The blunt force measurement system may include a blunt force sensor array configured to be subdermally implanted on a non-planar surface of a bone of a test subject, and measurement and control circuitry disposed external to the test subject and configured to interface with the blunt force sensor array to convert signals provided by the blunt force sensor array into force and strain measurements. The blunt force sensor array may include a flexible thin-film substrate secured to the non-planar surface of the bone, a plurality of force sensors secured to the flexible thin-film substrate proximate to a center measurement point, a strain gauge secured on the flexible thin-film substrate proximate to the center measurement point, and a sensor interface configured to connect to the measurement and control circuitry. The sensor interface may be electrically connected to each of the force sensors and the strain gauge via traces disposed on the flexible thin-film substrate. A flexibility and a shape of the flexible thin-film substrate may permit the blunt force sensor array to be applied to the non-planar surface to detect forces and strains experienced by the non-planar surface in response to a blunt force event on the non-planar surface.

According to some example embodiments, a method of subdermally implanting a blunt force sensor array in a test subject is provided. In this regard, the method may include making an incision in a dermal layer of the test subject, and applying a blunt force sensor array onto a non-planar surface of a bone of the test subject. The blunt force sensor array may include a central force sensor, a first peripheral force sensor, a second peripheral force sensor, and a strain gauge disposed on a flexible thin-film substrate. Applying the blunt force sensor array onto the non-planar surface includes applying the blunt force sensor array such that sensing areas of the central force sensor, the first peripheral force sensor, the second peripheral force sensor, and the strain gauge disposed on a flexible thin-film substrate are disposed in different planes.

BRIEF DESCRIPTION OF THE SEVERAL VIEWS OF THE DRAWINGS

Figure 1:
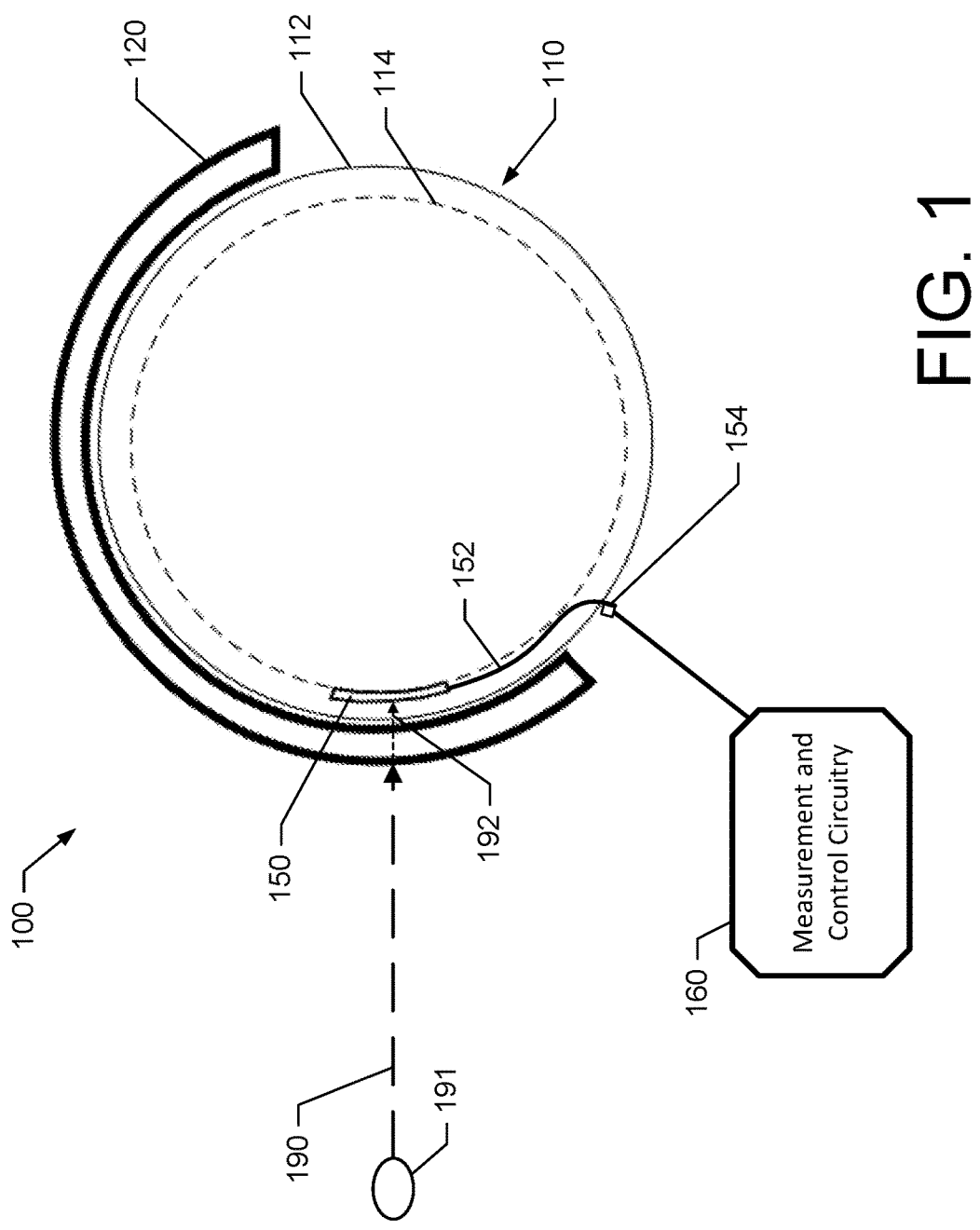
Figure 2:
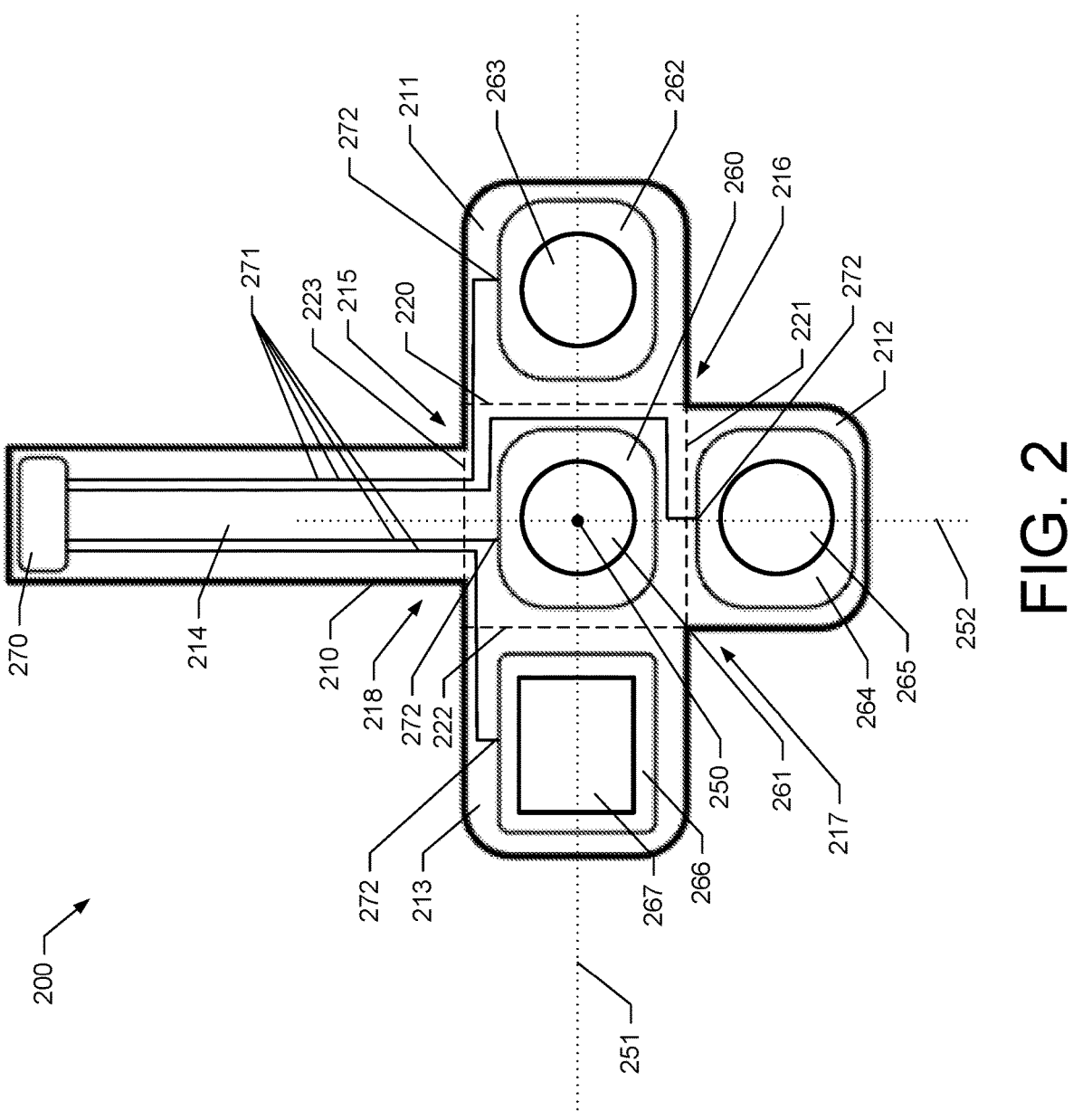
Figure 3:
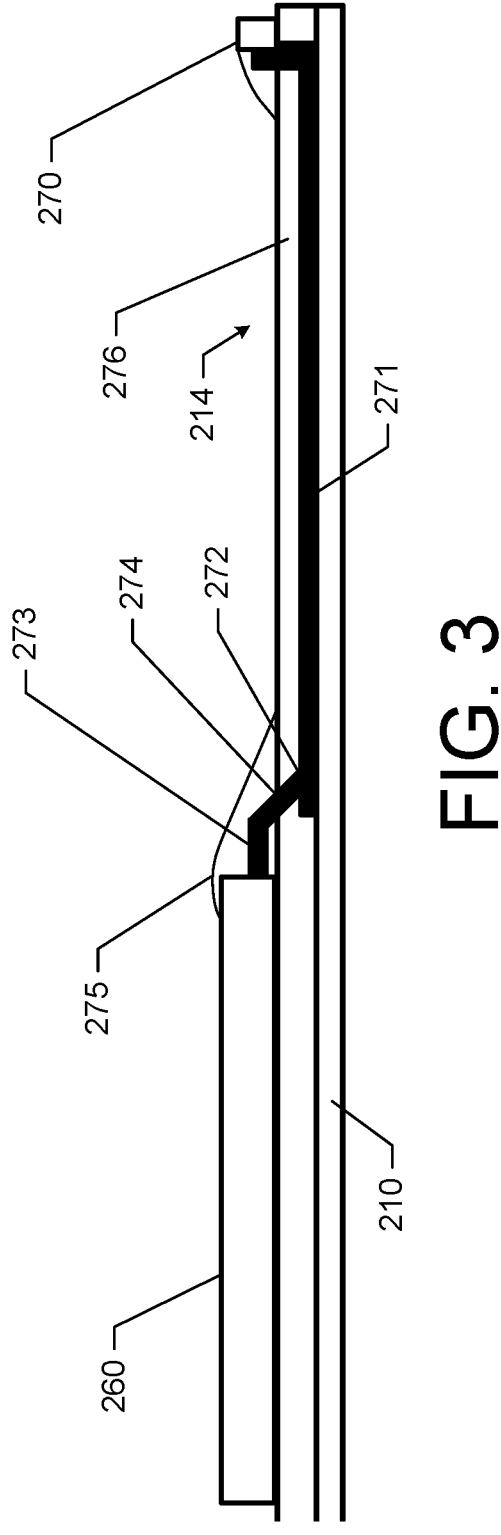
Figure 4:
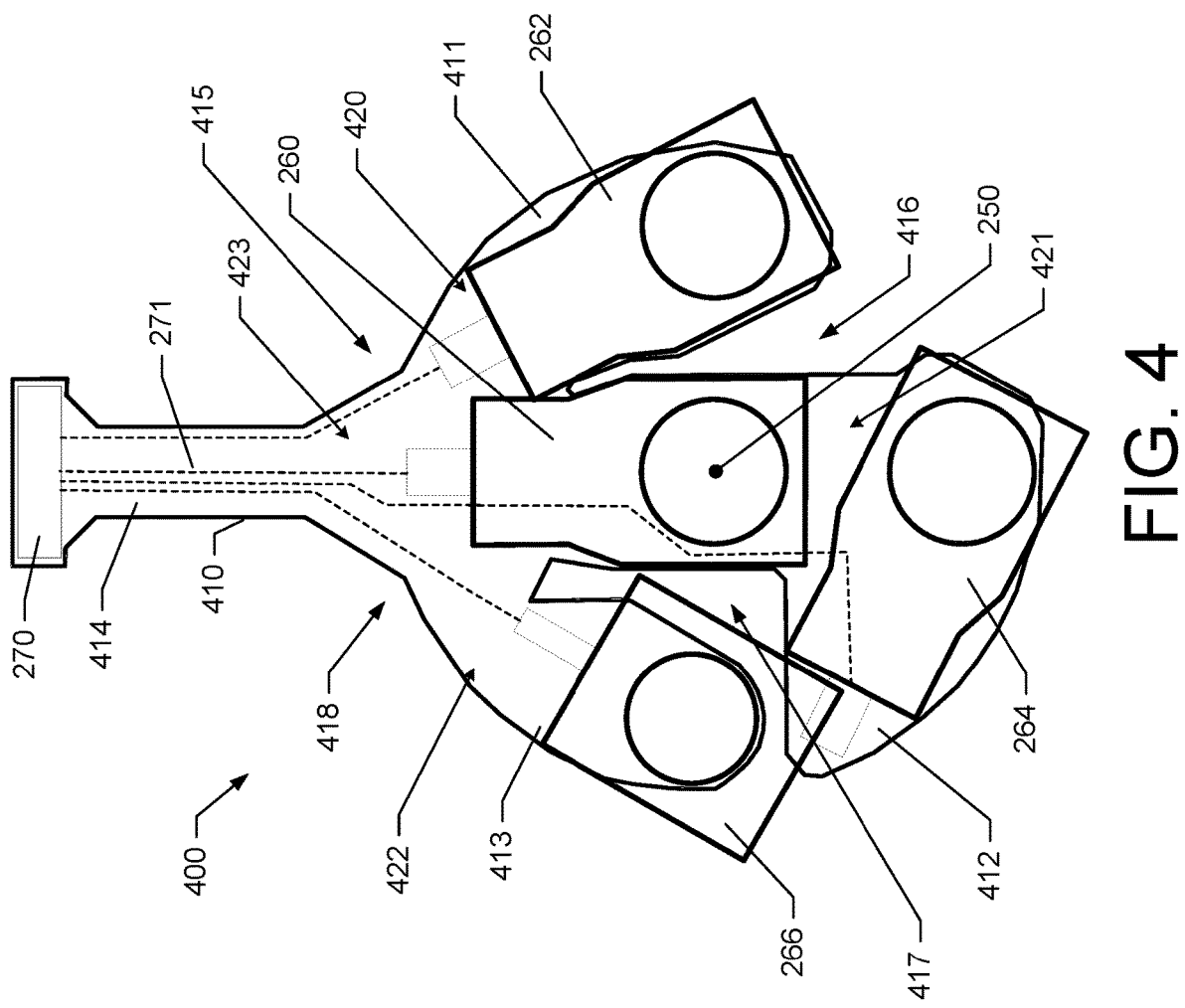
Figure 5:
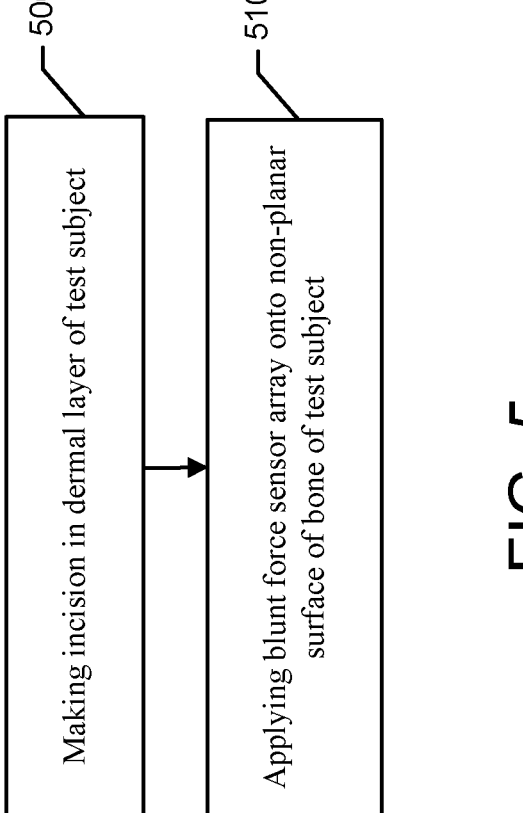

Having thus described some example embodiments in general terms, reference will now be made to the accompanying drawings, which are not necessarily drawn to scale, and wherein:

FIG. 1 illustrates an example behind helmet blunt trauma test environment according to some example embodiments;

FIG. 2 illustrates a top view of a blunt force sensor array according to some example embodiments;

FIG. 3 illustrates a side cross-section view of a blunt force sensor array according to some example embodiments;

FIG. 4 illustrates a top view of another blunt force sensor array according to some example embodiments; and FIG. 5 illustrates a block diagram of an example method for subdermally implanting a blunt force sensor array in a test subject according to some example embodiments.

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. As used herein, operable coupling should be understood to relate to direct or indirect connection that, in either case, enables functional interconnection of components that are operably coupled to each other.

According to various example embodiments, a blunt force sensor array and associated systems are provided. To be useful in a many space constrained environments the blunt force sensor array may be constructed on a flexible thin-film substrate. The thin-film substrate may provide a support structure upon which the blunt force sensor array may be constructed, while still permitting the array to conform to a non-planar surface (e.g., a sphere, the shape of a skull, or the like). Because a number of measurements at different locations may be useful to improve measurement accuracy and to determine force propagation, a plurality of force sensors may be included at different locations on the blunt force sensor array. Additionally, a strain gauge or strain sensor may also be included on the blunt force sensor array. According to some example embodiments, the sensors themselves may be thin (e.g., less than a millimeter scale) and may be formed as thin-film sensors for application to the flexible thin-film substrate. These sensors may be affixed (via an adhesive) to the flexible thin-film substrate in a defined arrangement, and that arrangement may be reproduced for use in a number of blunt force sensor arrays. In doing so, test repeatability can result due to the use of the array's common, unitary form factor. Because the spacing and placement of the sensors may be known, implementation of a blunt force sensor array within a test subject may simply require rotational orientation measurements relative to the center measurement point. As such, the flexible thin-film substrate may be used as an alignment key for placement of the blunt force sensor array during a procedure to simplify the placement procedure. This is an improvement over procedures that involve placement of individual sensors, which can add error to each placement in repeated tests.

According to some example embodiments, the flexibility and shape of the flexible thin-film substrate may permit the blunt force sensor array to be applied to a non-planar surface. Once applied, the blunt force sensor array may operate to detect forces (including strains) experienced by a non-planar surface to which the blunt force sensor array is applied. With respect to shape, the blunt force sensor array may include a number of flexible fingers with respective sensors. The fingers of the blunt force sensor array may be independently bendable at a base or bending region of the finger to permit the sensors to conform to a variety of surface shapes. Such non-planar surface shapes may include spherical shapes and non-uniform shapes such as the shape of a skull bone. In this way, the inclusion of the fingers of the flexible thin-film substrate permits the sensors to be positioned such that the sensors wrap around a region of a non-planar surface to support proper engagement of the sensors with the surface to be measured.

Such a blunt force sensor array may be useful in a number of different applications, including behind helmet blunt trauma (BHBT) testing. In such testing environments, the blunt force sensor array may be placed between the helmet and the skull of a cadaver or live subject (e.g., an animal such as a pig). According to some example embodiments, the blunt force sensor array may be subdermally implanted in the cadaver or live subject such that the flexible thin-film substrate and the sensors are in contact with or adhered to the skull bone surface to improve detection of the forces experienced by the skull bone in response to a blunt force test event. To satisfy the biological conditions of such a test, the blunt force sensor array, according to some example embodiments, may be sealed and waterproof to avoid the intrusion of fluids that may, for example, contact the electrical traces and affect signaling and transmission of data associated with sensor control and measurements.

Having described some example embodiments, reference will now be made to FIG. 1, which illustrates an example BHBT test environment 100. A helmet 120 is shown as applied to a test subject 110 having a dermal layer 112 and a skull surface 114. An example blunt force sensor array 150 may be applied beneath the dermal layer 112 and directly onto the skull surface 114, which may be a non-planer surface.

As mentioned above, the blunt force sensor array 150 may be implanted within the test subject via an incision location. Because the sensors of the blunt force sensor array 150 are affixed to the flexible thin-film substrate, all of the sensors may be placed with relative positioning based on the shape of the flexible thin-film substrate (rather than being separately positioned) thereby requiring a simpler placement procedure. As subtly shown in FIG. 1, the blunt force sensor array 150 conforms to the non-planar skull surface due to the flexibility of the substrate. A sensor interface extension or finger 152 of the flexible thin-film substrate may be extend a distance away from the sensors and pass out of the dermal layer 112 as a subcutaneous pass through to an external sensor interface 154.

The sensor interface 154 may include a coupler or a plug that facilitates an electrical connection to the measurement and control circuitry 160. The measurement and control circuitry 160 may be configured to receive and interpret sensor signals supplied by each of the sensors of the blunt force sensor array 150. The sensors of the blunt force sensor array 150 may include any type of sensors including force sensor strain gauges, or the like. For example, the sensors may be configured to output a voltage that is based on the force that is detected by the force sensors. Similarly, a strain gauge of the blunt force sensor array 150 may output a voltage that is based on the strain (e.g., compression or tension) that has been detected by the strain gauge. The measurement and control circuitry 160 may be configured to receive these voltage signals from the sensors and convert those signals into force measurement values in Newtons or the like and associated positions for analysis.

In this regard, the measurement and control circuitry 160 may embody or include processing circuitry that may be configurable to receive and interpret sensor signals. In this regard, the measurement and control circuitry 160 may include a processor, a memory, and various passive components for driving the sensors. According to some example embodiments, measurement and control circuitry 160 may be in operative communication with or embody, the memory and the processor. Through configuration and operation of the memory and the processor, the measurement and control circuitry 160 may be configurable to perform various operations as described herein, including the operations and functionalities described with respect to receipt, interpretation or conversion, and analysis of sensor signals. In this regard, the measurement and control circuitry 160 may be configured to perform computational processing, memory management, and sensor interface control and monitoring, according to some example embodiments. In some embodiments, the measurement and control circuitry 160 may be embodied as a chip or chip set. In other words, the measurement and control circuitry 160 may include one or more physical packages (e.g., chips) including materials, components or wires on a structural assembly (e.g., a baseboard). The measurement and control circuitry 160 may be configured to receive inputs (e.g., sensor signals via the sensor interface 154), perform actions based on the inputs, and generate outputs as described herein. In an example embodiment, the measurement and control circuitry 160 may include one or more instances of a processor, associated circuitry, and memory. Further, the measurement and control circuitry 160 may be embodied as a circuit chip [e.g., an integrated circuit chip, such as a field programmable gate array (FPGA)] configured (e.g., with hardware, software or a combination of hardware and software) to perform operations described herein.

In an example embodiment, the memory of the measurement and control circuitry 160 may include one or more non-transitory memory devices such as, for example, volatile or non-volatile memory that may be either fixed or removable. The memory may be configured to store information, data, applications, instructions or the like for enabling, for example, the functionalities described with respect to the measurement and control circuitry 160. The memory may operate to buffer instructions and data during operation of the measurement and control circuitry 160 to support higher-level functionalities, and may also be configured to store instructions for execution by the measurement and control circuitry 160. The memory may also store various information including conversion algorithms. According to some example embodiments, various data stored in the memory may be generated based on other data and stored or the data may be retrieved.

As mentioned above, the measurement and control circuitry 160 may be embodied in a number of different ways. For example, the measurement and control circuitry 160 may be embodied as various processing means such as one or more processors that may be in the form of a microprocessor or other processing element, a coprocessor, a controller or various other computing or processing devices including integrated circuits such as, for example, an ASIC (application specific integrated circuit), an FPGA, or the like. In an example embodiment, the measurement and control circuitry 160 may be configured to execute instructions stored in the memory or otherwise accessible to the measurement and control circuitry 160. As such, whether configured by hardware or by a combination of hardware and software, the measurement and control circuitry 160 may represent an entity (e.g., physically embodied in circuitry—in the form of measurement and control circuitry 160) capable of performing operations according to example embodiments while configured accordingly. Thus, for example, when the measurement and control circuitry 160 is embodied as an ASIC, FPGA, or the like, the measurement and control circuitry 160 may be specifically configured hardware for conducting the operations described herein. Alternatively, as another example, when the measurement and control circuitry 160 is embodied as an executor of software instructions, the instructions may specifically configure the measurement and control circuitry 160 to perform the operations described herein.

With the measurement and control circuitry 160 configured according to various example embodiments, the BHBT test environment 100 may be configured to perform a test operation. In this regard, a projectile 191 may be fired or launched at the helmet 120 in alignment with the blunt force sensor array 150. In this regard, prior to being fired or launched, the path 190 of the projectile 191 may be aligned with a measurement center point for the blunt force sensor array 150. Upon impact with the helmet 120, forces in the projectile 191 may be transferred to the helmet 120. While the helmet 120 may dissipate some of the forces of the impact, some forces may be transferred through the helmet 120 to the test subject 110 and the skull surface 114 as indicated by arrow 192. The forces and strains that reach the skull surface 114 may be measured by the sensors of the blunt force sensor array 150. Sensor signals may be provided via the sensor interface 154 in real time (with the exception of circuitry delays) to the measurement and control circuitry 160 for storage and/or analysis. According to some example embodiments, the measurement and control circuitry 160 may be configured to analyze the sensor signals to construct a map of the intensities of the forces and strains over time. The analysis of the sensor signals may also be used to the determine potential health effects of the projectile impact on the helmet 120 (e.g., likelihood of a concussion, loss of consciousness, brain cell bruising, torn tissue, bleeding, and other physical damage to the brain).

Having described a test environment and implementation of an example blunt force sensor array, FIGS. 2 to 4 will now be described which show example constructions of blunt force sensor arrays according to some example embodiments. It is understood that the layouts and positioning of the sensors in the blunt force sensor arrays described herein are exemplary. However, the inclusion of extended portions or fingers facilitates an ability to move or bend the sensors into different relative positions to conform the sensing areas of the sensors in to close engagement with a non-planar surface.

Now referring specifically to FIG. 2, a blunt force sensor array 200 is shown that may be the same or similar to the blunt force sensor array 150 of FIG. 1. In general, the blunt force sensor array 200 may include a flexible thin-film substrate 210, a plurality of force sensors (e.g., center force sensor 260, first peripheral force sensor 262, and second peripheral force sensor 264), and a strain gauge 266. The blunt force sensor array 200 may also include a sensor interface 270. The sensor interface 270 may be a coupler or connector to electrically connect the blunt force sensor array 200 to external measurement and control circuitry. According to some example embodiments, the sensor interface 270 may include a connector (e.g., a twelve pin connector).

The flexible thin-film substrate 210 may include a flexible supportive substance that may be supplied as a sheet for cutting out a desired design for the flexible thin-film substrate 210. According to some example embodiments, the flexible thin-film substrate 210 may include a polyamide film (e.g., KAPTON®) and may include a metallic layer that may be included or added and etched to form traces 271 of a circuit. According to some example embodiments, the flexible thin-film substrate 210 may be PYRALUX® LF-series flexible circuit board substrate.

The layout of the flexible thin-film substrate 210 may include a plurality of extensions or fingers. Each finger of the flexible thin-film substrate 210 may have at least one force sensor, a strain gauge, or the sensor interface 270 affixed thereto. In this regard, the flexible thin-film substrate 210 may include, for example, four fingers that generally extend away from a center region in a radial manner. To form the fingers, voids may be cut between the fingers. As such, the flexible thin-film substrate 210 may include a first finger 211 to which the first peripheral force sensor 262 is affixed, a second finger 212 to which the second peripheral force sensor 264 is affixed, a third finger 213 to which the strain gauge 266 is affixed, and a fourth finger 214 to which the sensor interface 270 is affixed. As mentioned above, to form the fingers void 215 may be disposed between the fourth finger 214 and the first finger 211, void 216 may be disposed between the first finger 211 and the second finger 212, void 217 may be disposed between the second finger 212 and the third finger 213, and void 218 may be disposed between the third finger 213 and the fourth finger 214.

The cutting of the voids can form natural bend lines or regions at a base of each finger where the fingers are most likely to bend. In a substantially symmetric design of the flexible thin-film substrate 210, bend lines 220, 221, 222, and 223 are formed between apexes of the voids. The bend lines allow for bending in addition to the substrate 210 being flexible which permits bending elsewhere as well. As such, if applied to a non-planar surface, the first finger 211 may bend about the bend line 220, the second finger 212 may bend about the bend line 221, the third finger 213 may bend about the bend line 222, and the fourth finger 214 may bend about the bend line 222. As mentioned earlier, such bend lines are not the only bending that the flexible thin-film substrate 210 may perform, but the existence of the voids tends to create such natural bend lines or bend regions. As such, differently shaped fingers and voids may result is different bend lines and regions. In any event, the fingers 211, 212, 213, and 214 may have an ability to bend independent of each other at these bend lines or regions to conform the sensors to a non-planar or non-uniform surface.

According to some example embodiments, the blunt force sensor array 200 may include a plurality of force sensors. In the example embodiment shown FIG. 2, the blunt force sensor array 200 includes three force sensors, i.e., the central force sensor 260, the first peripheral force sensor 262, and the second peripheral force sensor 264. According to some example embodiments, each of these force sensors may be identically constructed, but placed at different locations on the flexible thin-film substrate 210. For example, the central force sensor 260 may be a thin film force sensor with a thickness of less than 0.25 millimeters. As such, a thickness of the blunt force sensor array 200 at any of the sensing areas of the plurality of force sensors may be less than about 0.5 millimeters. According to some example embodiments, a voltage biasing scheme may be applied to the central force sensor 260 to determine a range of forces that the sensor is configured to detect. The central force sensor 260 may change a characteristic value (e.g., electrical resistance) when a force is applied to the sensor. Based on the test or application for the blunt force sensor array 200, an appropriate voltage-biasing scheme may be used. According to some example embodiments, the change in electrical resistance may be indicated in a voltage of a signal that is provided by the central force sensor 260 to the sensor interface 270. The central force sensor 260 may have a sensing area 261. The sensing area 261 may be an area where a measurement of force is taken for a force applied to the sensing area 261. According to some example embodiments, the central force sensor 260 may be a TEKSCAN® FLEXIFORCE® sensor A301. As mentioned above, the first peripheral force sensor 262 and the second peripheral force sensor 264 may be the same or similar to the central force sensor 260. In this regard, the first peripheral force sensor 262 may have a sensing area 263 and the second peripheral force sensor 264 may have a sensing area 265.

The strain gauge 266 may be configured to measure compression or tension in the surface to which the strain gauge 266 is affixed. According to some example embodiments, the strain gauge 266 may be a triaxial strain gauge. More specifically, according to some example embodiments, the strain gauge 266 may be a KYOWA® KFW strain gauge. The strain gauge 266 may change a characteristic value (e.g., electrical resistance) when a strain is applied to the gauge. According to some example embodiments, the change in electrical resistance may be indicated in a voltage of a signal that is provided by the strain gauge 266 to the sensor interface 270. Similar to the force sensors, the strain gauge 266 may have a sensing area 267.

The sensors may be electrically connected to the sensor interface 270 via traces 271. The traces 271 may be formed from a thin layer of metal (e.g., copper) that may be etched to define the traces 271. The traces 271 may carry a control and/or output signal for each of the sensors. In this regard, FIG. 3 shows a cross-section of the blunt force sensor array 200 taken from the sensor interface 270 to the central force sensor 260 along the fourth finger 214. As can be seen in FIG. 3, the trace 271 sits atop the flexible thin-film substrate 210. Additionally, according to some example embodiments, a protecting thin film layer 276 may be applied over the traces 271 to protect and waterproof the traces 271. The traces 271 may be connected to the respective sensors at connection points 272 (FIGS. 2 and 3). In this regard, the traces 271 may form a pad at the connection points 272 and the pins of the sensors, for example, may be soldered to the pads to form the connections. As shown in FIG. 3, the pin 273 of central force sensor 260 is connected to trace 271 at connection point 272 via solder 274. According to some example embodiments, the soldered connection points 272 may be encapsulated with an insulating substance 276 to seal and waterproof the connection points 272. The configuration of the connection point 272 in FIG. 3 is provided as an example how the other connection points 272 may also be embodied.

Referring back to FIG. 2, a description of the placement of the sensors and fingers for the blunt force sensor array 200 will now be provided. In this regard, according to some example embodiments, the plurality of force sensors 260, 262, and 264 may be secured to the flexible thin-film substrate 210 proximate to a center measurement point 250. Similarly, the strain gauge 266 may be secured on the flexible thin-film substrate 210 proximate to the center measurement point 250. In this regard, according to some example embodiments, the central force sensor 260 may be disposed such that the center measurement point 250 is centrally located within the sensing area 261 of the central force sensor 260. According to some example embodiments, the center measurement point 250 may be a location that, in a test environment implementation, is aligned with an impact force, for example, delivered by a projectile.

With respect the positioning of the components of the blunt force sensor array 200, it is noted that the blunt force sensor array 200 is shown in a flat, planar configuration. While not intended to be applied to a flat surface, the relative positions of the components of the blunt force sensor array 200 may be described while in such as configuration. In this regard, when flat, sensing areas of the first peripheral force sensor 262, the second peripheral force sensor 264, and the strain gauge 266 may be disposed a common radial distance away from the center measurement point 250. Additionally, according to some example embodiments, the sensor interface 270 may be disposed a distance, i.e., a sensor interface distance, from the center measurement point 250. The sensor interface distance may be larger than the common radial distance for the sensors, for example, to limit an effect of the external connections to the sensor interface 270 on measurements performed by the plurality of force sensors and the strain gauge. Additionally, the fourth finger 214 may be used as a subcutaneous pass through, when the blunt force sensor array 200 is implanted into a test subject, and the added length may facilitate such a pass through. In this regard, the sensor interface 270 may be disposed external to the test subject, while the remainder of the blunt force sensor array 200 may be subdermally implanted, for example, onto a bone (e.g., the skull).

Additionally, the peripheral force sensors 262 and 264 and the strain gauge 266 may be disposed at the distal ends of their respective fingers (with the opposite proximal ends being more centrally located). In this regard, the first peripheral force sensor 262 may be disposed at a distal end of a first finger 211 and the second peripheral force sensor 264 may be disposed at a distal end of the second finger 212. Additionally, the strain gauge 266 may be disposed at a distal end of a third finger 213. Further, according to some example embodiments, the sensing areas of the central force sensor 260, the first peripheral force sensor 262, and the strain gauge 266 may be in a linear alignment (as indicated by line 251) when the flexible thin-film substrate 210 is flat. Additionally, the second peripheral force sensor 264 may be positioned on a line 252 through the center measurement point 250 that is perpendicular to line 251. Such linear alignments and relative positioning may assist with data analysis and alignment for determining the positions of force measurements and strain measurements, for example, to map the positions of the forces and strains on the non-planar surface being evaluated.

Due to the positioning of the plurality of force sensors and the strain gauge on the flexible thin-film substrate 210, the blunt force sensor array 200 may be flexed and bent into a shape that conforms with a non-planar surface, such that the plurality of force sensors and the strain gauge are in close engagement with the non-planar surface to measure forces and strains. Additionally, according to some example embodiments, the voids between the first finger, the second finger, and the third finger operate to permit each of the first finger, the second finger, and the third finger to be bent about at a respective finger base and an associated bend line or region relative to each other to conform the blunt force sensor array to a non-planar surface.

Now referring to FIG. 400 another blunt force sensor array 400 is shown that includes the components of the blunt force sensor array 200 (the same reference numerals refer to the same components), however with a differently shaped flexible thin-film substrate 410. The flexible thin-film substrate 410 may be formed in the same or similar manner as the flexible thin-film substrate 210, however with a different cut shape. Further, in the construction of the blunt force sensor array 400, the packaging of the sensors of the array 400 may be clipped or cut to reduce the size of the sensors and thus the blunt force sensor array 400.

As can be seen in FIG. 4, the fingers 411, 412, and 413 of the flexible thin-film substrate 410 for the sensors are cut from a substantially circular lower portion (i.e., sensor section) of the flexible thin-film substrate 410 with a finger 414 for the sensor interface 270 extending upwards. According to some example embodiments, a diameter of the substantially circular lower portion may be about 5 centimeters. The first finger 411 forms an extension upon which the first peripheral force sensor 262 is affixed with a sensor area at the first finger's distal end. The cutting of void 415 between the fourth finger 414 and the first finger 411 and void 415 between the first finger 411 and the second finger 412 can create a natural bending region 420 where the first finger 411 may bend to conform to a non-planar surface.

The second finger 412 forms an extension upon which the second peripheral force sensor 264 is affixed with a sensor area at the second finger's distal end. The cutting of void 416 between the first finger 411 and the second finger 412 and void 417 between the second finger 412 and the third finger 413 can create a natural bending region 421 where the second finger 411 may bend to conform to a non-planar surface. The voids 416 and 417 also extend inwards to be adjacent to the central force sensor 260. As such, the second finger 412 may have a natural bending region near an intersection of the fingers. Note also that, to maintain a small footprint for the flexible thin-film substrate 410, the orientation of the pins of second peripheral force sensor 264 is rotated to the left. By rotating the sensor 264 in this way, the overall layout of the flexible thin-film substrate 410 remains compact while also lessening a length of the traces 271 that feed the second peripheral force sensor 264 (i.e. the most distant sensor from the sensor interface 270).

The third finger 413 forms an extension upon which the strain gauge 266 is affixed with a sensor area at the third finger's distal end. The cutting of void 417 between the second finger 412 and the third finger 413 and void 418 between the third finger 413 and the fourth finger 414 can create a natural bending region 422 where the third finger 413 may bend to conform to a non-planar surface. Finally, the fourth finger 414 forms an extension upon which the sensor interface 270 is affixed at the fourth finger's distal end. The cutting of void 418 between the third finger 413 and the fourth finger 414 and void 415 between the fourth finger 414 and the first finger 411 can create a natural bending region 423 where the fourth finger 414 may bend to conform to a non-planar surface.

Note that the characteristics (angles, depths, widths, etc.) of the voids between the fingers may determine where and how the fingers may naturally bend. According to some example embodiments, the non-planar surface or the types of non-planar surfaces to which the blunt force sensor array 400 is to be affixed may be analyzed to determine characteristics for the voids that form the fingers (angles, depths, widths, etc.). In this regard, depending on the curvature and/or common features on the non-planar surface, the voids may be determined improve engagement of the sensors with the non-planar for improved measurements.

Now referring to FIG. 5, a method for subdermally implanting a blunt force sensor array in a test subject is provided. The blunt force sensor array to be implanted may be the blunt force sensor array 150, 200, or 400, and variations thereof as described herein. In this regard, the example method may include, at 500, making an incision in a dermal layer of the test subject. The incision is made to provide access to the bone structures to which the blunt force sensor array will be affixed or placed near. Subsequently, at 510, the example method may include applying the blunt force sensor array onto a non-planar surface of a bone (e.g., a skull) of the test subject. As mentioned above, the blunt force sensor array may be the same or similar to the blunt force sensor array 150, 200, or 400. In this regard, the blunt force sensor array may include a central force sensor, a first peripheral force sensor, a second peripheral force sensor, and a strain gauge disposed on a flexible thin-film substrate. Further, according to some example embodiments, applying the blunt force sensor array onto a non-planar surface may also include applying the blunt force sensor array such that sensing areas of the central force sensor, the first peripheral force sensor, the second peripheral force sensor, and the strain gauge disposed on a flexible thin-film substrate are on different planes. In this regard, the flexibility of the blunt force sensor array may permit the sensor and, more specifically, the sensing areas of the sensors to be engaged to be bent into positions such that the sensing areas are oriented in different planes (e.g., the sensing areas are engaged with respective positions on a generally spherical shape such as a skull bone).

As such, the following provides a description of some example embodiments in light of the subject matter included herein. In this regard, a blunt force sensor array for application to a non-planar surface is provided. The blunt force sensor array may include a flexible thin-film substrate, a plurality of force sensors secured to the flexible thin-film substrate proximate to a center measurement point, a strain gauge secured on the flexible thin-film substrate proximate to the center measurement point, and a sensor interface configured to connect to external measurement and control circuitry. The sensor interface may be electrically connected to each of the force sensors and the strain sensor via traces disposed on the flexible thin-film substrate. A flexibility and a shape of the flexible thin-film substrate permits the blunt force sensor array to be applied to the non-planar surface to detect forces and strains experienced by the non-planar surface in response to a blunt force event on the non-planar surface.

According to some example embodiments, the plurality of force sensors may include a central force sensor, a first peripheral force sensor, and a second peripheral force sensor. The sensing area of the central force sensor may be disposed at the center measurement point. The sensing areas of the first peripheral force sensor, the second peripheral force sensor, and the strain gauge may be disposed a common radial distance away from the center measurement point when the flexible thin-film substrate is flat. According to some example embodiments, the first peripheral force sensor may be disposed at a distal end of a first finger of the flexible thin-film substrate. The second peripheral force sensor may be disposed at a distal end of a second finger of the flexible thin-film substrate. The strain gauge may be disposed at a distal end of a third finger of the flexible thin-film substrate. The flexible thin-film substrate may include voids between the first finger, the second finger, and the third finger to permit each of the first finger, the second finger, and the third finger to bend about at a respective finger base relative to each other to conform the blunt force sensor array to the non-planar surface. According to some example embodiments, sensing areas of the first peripheral force sensor, the second peripheral force sensor, and the strain gauge may be disposed a common radial distance away from the center measurement point. The sensor interface may be disposed at a distal end of a fourth finger of the flexible thin-film substrate. The sensor interface may be disposed a sensor interface distance from the center measurement point. The sensor interface distance may be larger than the common radial distance to limit an effect of external connections to the sensor interface on measurements performed by the plurality of force sensors and the strain gauge. According to some example embodiments, the plurality of force sensors may include a central force sensor, a first peripheral force sensor, and a second peripheral force sensor. Sensing areas of the central force sensor, the first peripheral force sensor, and the strain gauge may be in a linear alignment when the flexible thin-film substrate is flat. According to some example embodiments, the traces may be disposed on the flexible thin-film substrate and covered by a protecting film layer. According to some example embodiments, electrical connection points between the plurality of force sensors and the traces may be encapsulated by a waterproof substance to waterproof the blunt force sensor array. According to some example embodiments, the blunt force sensor array may be configured to operate as a subdermal implant that is affixed to bone. According to some example embodiments, each of the plurality of force sensors may include a sensing area. Additionally, a thickness of the blunt force sensor array at any of the sensing areas may be less than about 0.5 millimeters.

According to some example embodiments, a blunt force measurement system is provided. The blunt force measurement system may include a blunt force sensor array configured to be subdermally implanted on a non-planar surface of a bone of a test subject, and measurement and control circuitry disposed external to the test subject and configured to interface with the blunt force sensor array to convert signals provided by the blunt force sensor array into force and strain measurements. The blunt force sensor array may include a flexible thin-film substrate secured to the non-planar surface of the bone, a plurality of force sensors secured to the flexible thin-film substrate proximate to a center measurement point, a strain gauge secured on the flexible thin-film substrate proximate to the center measurement point, and a sensor interface configured to connect to the measurement and control circuitry. The sensor interface may be electrically connected to each of the force sensors and the strain sensor via traces disposed on the flexible thin-film substrate. A flexibility and a shape of the flexible thin-film substrate may permit the blunt force sensor array to be applied to the non-planar surface to detect forces and strains experienced by the non-planar surface in response to a blunt force event on the non-planar surface. According to some example embodiments, the plurality of force sensors may include a central force sensor, a first peripheral force sensor, and a second peripheral force sensor. A sensing area of the central force sensor may be disposed at the center measurement point. Sensing areas of the first peripheral force sensor, the second peripheral force sensor, and the strain gauge may be disposed a common radial distance away from the center measurement point when the flexible thin-film substrate is flat. According to some example embodiments, the plurality of force sensors may include a central force sensor, a first peripheral force sensor, and a second peripheral force sensor. The first peripheral force sensor may be disposed at a distal end of a first finger of the flexible thin-film substrate. The second peripheral force sensor may be disposed at a distal end of a second finger of the flexible thin-film substrate. A strain gauge may be disposed at a distal end of a third finger of the flexible thin-film substrate. The flexible thin-film substrate may include voids between the first finger, the second finger, and the third finger to permit each of the first finger, the second finger, and the third finger to bend about at a respective finger base relative to each other to conform the blunt force sensor array to the non-planar surface. According to some example embodiments, sensing areas of the first peripheral force sensor, the second peripheral force sensor, and the strain gauge may be disposed a common radial distance away from the center measurement point. The sensor interface may be disposed at a distal end of a fourth finger of the flexible thin-film substrate. The sensor interface may be disposed a sensor interface distance from the center measurement point. The sensor interface distance may be larger than the common radial distance to limit an effect of external connections to the sensor interface on measurements performed by the plurality of force sensors and the strain gauge.

According to some example embodiments, the plurality of force sensors may include a central force sensor, a first peripheral force sensor, and a second peripheral force sensor. Sensing areas of the central force sensor, the first peripheral force sensor, and the strain gauge may be in a linear alignment when the flexible thin-film substrate is flat. According to some example embodiments, the traces may be disposed on the flexible thin-film substrate and covered by a protecting film layer. Electrical connection points between the plurality of force sensors and the traces may be encapsulated by a waterproof substance to waterproof the blunt force sensor array. According to some example embodiments, each of the plurality of force sensors may include a sensing area. A thickness of the blunt force sensor array at any of the sensing areas is less than about 0.5 millimeters.

According to some example embodiments, a method for subdermally implanting a blunt force sensor array in a test subject is provided. The method may include making an incision in a dermal layer of the test subject, and applying a blunt force sensor array onto a non-planar surface of a bone of the test subject. The blunt force sensor array may include a central force sensor, a first peripheral force sensor, a second peripheral force sensor, and a strain gauge disposed on a flexible thin-film substrate. Applying the blunt force sensor array onto the non-planar surface may include applying the blunt force sensor array such that sensing areas of the central force sensor, the first peripheral force sensor, the second peripheral force sensor, and the strain gauge, disposed on a flexible thin-film substrate, are disposed in different planes. According to some example embodiments, the first peripheral force sensor may be disposed at a distal end of a first finger of the flexible thin-film substrate. The second peripheral force sensor may be disposed at a distal end of a second finger of the flexible thin-film substrate. The strain gauge may be disposed at a distal end of a third finger of the flexible thin-film substrate. The flexible thin-film substrate may include voids between the first finger, the second finger, and the third finger to permit each of the first finger, the second finger, and the third finger to bend about at a respective finger base relative to each other to conform the blunt force sensor array to the non-planar surface. According to some example embodiments, each of the plurality of force sensors include a sensing area. A thickness of the blunt force sensor array at any of the sensing areas may be less than about 0.5 millimeters.

Many modifications and other embodiments of the measuring device set forth herein will come to mind to one skilled in the art to which these inventions pertain having the benefit of the teachings presented in the foregoing descriptions and the associated drawings. Therefore, it is to be understood that the measuring devices are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A blunt force sensor array for subdermal application to a non-planar surface of a bone, the blunt force sensor array comprising:

a flexible thin-film substrate comprising independently bendable fingers, wherein the independently bendable fingers comprise a first finger, a second finger, a third finger, and a fourth finger;

a plurality of force sensors secured to the flexible thin-film substrate proximate to a center measurement point;

a strain gauge secured on the flexible thin-film substrate proximate to the center measurement point, wherein at least one of the force sensors or the strain gauge is disposed at a distal end of each independently bendable finger; and a sensor interface configured to extend through an incision in a dermal layer to externally connect to external measurement and control circuitry, the sensor interface being electrically connected to each of the force sensors and the strain gauge via traces disposed on the flexible thin-film substrate, wherein a flexibility and a shape of the flexible thin-film substrate and the independently bendable fingers permit the blunt force sensor array to be inserted subdermally through the incision in a dermal layer such that each independently bendable finger and the force sensor or strain gauge secured thereon conform to and are in contact with the non-planar surface of the bone to detect subdermal forces and strains experienced by the non-planar surface of the bone, due to a blunt force event that originates external to the dermal layer, at a respective location on the bone;

wherein each of the independently bendable fingers extend from a common bending region;

wherein the sensor interface, the center measurement point, and the common bending region are aligned along a linear relationship;

wherein the first finger extends from the common bending region at a non-perpendicular angle to the linear relationship to conform to a curvature of the non-planar surface of the bone and place a peripheral force sensor secured at a distal end of the first finger in contact with the bone.

2. The blunt force sensor array of claim 1, wherein the peripheral force sensor is a first peripheral force sensor, the plurality of force sensors comprises a central force sensor, athe first peripheral force sensor, and a second peripheral force sensor, a sensing area of the central force sensor is disposed at the center measurement point, and sensing areas of the first peripheral force sensor, the second peripheral force sensor, and the strain gauge are disposed a common radial distance away from the center measurement point when the flexible thin-film substrate is flat.

3. The blunt force sensor array of claim 1, wherein the peripheral force sensor is a first peripheral force sensor, the plurality of force sensors comprise a central force sensor, athe first peripheral force sensor, and a second peripheral force sensor, the second peripheral force sensor is disposed at a distal end of athe second finger of the flexible thin-film substrate, the strain gauge is disposed at a distal end of thea third finger of the flexible thin-film substrate, and the flexible thin-film substrate comprises voids among the first finger, the second finger, and the third finger to permit each of the first finger, the second finger, and the third finger to bend about at a respective finger base relative to each other to conform the blunt force sensor array to the non-planar surface.

4. The blunt force sensor array of claim 3, wherein sensing areas of the first peripheral force sensor, the second peripheral force sensor, and the strain gauge are disposed a common radial distance away from the center measurement point when the flexible thin-film substrate is flat, the sensor interface is disposed at a distal end of athe fourth finger of the flexible thin-film substrate, and the sensor interface is disposed a sensor interface distance from the center measurement point, the sensor interface distance being larger than the common radial distance to limit an effect of external connections to the sensor interface on measurements performed by the plurality of force sensors and the strain gauge.

5. The blunt force sensor array of claim 1, wherein the peripheral force sensor is a first peripheral force sensor, the plurality of force sensors comprise a central force sensor, the first peripheral force sensor, and a second peripheral force sensor, and sensing areas of the central force sensor, the first peripheral force sensor, and the strain gauge are in a linear alignment when the flexible thin-film substrate is flat.

6. The blunt force sensor array of claim 1, wherein the traces are disposed on the flexible thin-film substrate and covered by a protecting film layer.

7. The blunt force sensor array of claim 1, wherein electrical connection points between the plurality of force sensors and the traces are encapsulated by a waterproof substance to waterproof the blunt force sensor array.

8. The blunt force sensor array of claim 1, wherein each of the plurality of force sensors comprise a sensing area, and a thickness of the blunt force sensor array at any of the sensing areas is less than about 0.5 millimeters.

9. The blunt force sensor array of claim 1, wherein the blunt force sensor array is configured to be implemented in a test environment where an impact force of the blunt force event is aligned with the center measurement point.

10. A blunt force measurement system comprising:

a blunt force sensor array configured to be subdermally implanted on a non-planar surface of a bone of a test subject; and measurement and control circuitry disposed external to the test subject and configured to interface with the blunt force sensor array to convert signals provided by the blunt force sensor array into force and strain measurements, wherein the blunt force sensor array comprises:

a flexible thin-film substrate comprising independently bendable fingers, wherein the independently bendable fingers comprise a first finger, a second finger, a third finger, and a fourth finger;

a plurality of force sensors secured to the flexible thin-film substrate proximate to a center measurement point;

a strain gauge secured on the flexible thin-film substrate proximate to the center measurement point, wherein at least one of the force sensors or the strain gauge is disposed at a distal end of each independently bendable finger; and a sensor interface configured to extend through an incision in a dermal layer to externally connect to the measurement and control circuitry, the sensor interface being electrically connected to each of the force sensors and the strain gauge via traces disposed on the flexible thin-film substrate;

wherein a flexibility and a shape of the flexible thin-film substrate and the independently bendable fingers permit the blunt force sensor array to be inserted subdermally through the incision in the dermal layer such that each independently bendable finger and the force sensor or strain gauge secured thereon conform to and are in contact with the non-planar surface of the bone to detect forces and strains experienced by the non-planar surface of the bone, due to a blunt force event that originates external to the dermal layer, at a respective location on the bone;

wherein each of the independently bendable fingers extend from a common bending region;

wherein the sensor interface, the center measurement point, and the common bending region are aligned along a linear relationship;

wherein the first finger extends from the common bending region at a non-perpendicular angle to the linear relationship to conform to a curvature of the non-planar surface of the bone and place a peripheral force sensor secured at a distal end of the first finger in contact with the bone.

11. The blunt force measurement system of claim 10, wherein the peripheral force sensor is a first peripheral force sensor, the plurality of force sensors comprise a central force sensor, the first peripheral force sensor, and a second peripheral force sensor, a sensing area of the central force sensor is disposed at the center measurement point, and sensing areas of the first peripheral force sensor, the second peripheral force sensor, and the strain gauge are disposed a common radial distance away from the center measurement point when the flexible thin-film substrate is flat.

12. The blunt force measurement system of claim 10, wherein the peripheral force sensor is a first peripheral force sensor, the plurality of force sensors comprise a central force sensor, a first peripheral force sensor, and a second peripheral force sensor, wherein the second peripheral force sensor is disposed at a distal end of thea second finger of the flexible thin-film substrate, the strain gauge is disposed at a distal end of the third finger of the flexible thin-film substrate, and the flexible thin-film substrate comprises voids among the first finger, the second finger, and the third finger to permit each of the first finger, the second finger, and the third finger to bend about at a respective finger base relative to each other to conform the blunt force sensor array to the non-planar surface.

13. The blunt force measurement system of claim 12, wherein sensing areas of the first peripheral force sensor, the second peripheral force sensor, and the strain gauge are disposed a common radial distance away from the center measurement point, the sensor interface is disposed at a distal end of a the fourth finger of the flexible thin-film substrate, and the sensor interface is disposed a sensor interface distance from the center measurement point, the sensor interface distance being larger than the common radial distance to limit an effect of external connections to the sensor interface on the force and strain measurements performed by the plurality of force sensors and the strain gauge.

14. The blunt force measurement system of claim 10, wherein the peripheral force sensor is a first peripheral force sensor, the plurality of force sensors comprise a central force sensor, athe first peripheral force sensor, and a second peripheral force sensor, and sensing areas of the central force sensor, the first peripheral force sensor, and the strain gauge are in a linear alignment when the flexible thin-film substrate is flat.

15. The blunt force measurement system of claim 10, wherein the traces are disposed on the flexible thin-film substrate and covered by a protecting film layer.

16. The blunt force measurement system of claim 10, wherein electrical connection points between the plurality of force sensors and the traces are encapsulated by a waterproof substance to waterproof the blunt force sensor array.

17. The blunt force measurement system of claim 10, wherein each of the plurality of force sensors comprise a sensing area, and a thickness of the blunt force sensor array at any of the sensing areas is less than about 0.5 millimeters.

18. A method of subdermally implanting a blunt force sensor array in a test subject, the method comprising:

making an incision in a dermal layer of the test subject; and applying a plurality of force sensors and a strain gauge disposed on a thin film substrate of the blunt force sensor array subdermally, through the incision in the dermal layer, onto a non-planar surface of a bone of the test subject, wherein the plurality of force sensors comprises a central force sensor, a first peripheral force sensor, a second peripheral force sensor, wherein the plurality of force sensors and the strain gauge are applied such that sensing areas of the central force sensor, the first peripheral force sensor, the second peripheral force sensor, and the strain gauge, disposed on the flexible thin-film substrate, are disposed in different planes;

wherein a flexibility and a shape of the flexible thin-film substrate and independently bendable fingers of the flexible thin film substrate permit the blunt force sensor array to be inserted subdermally through the incision in the dermal layer such that each independently bendable finger and the force sensor or strain gauge secured thereon conform to and are in contact with the non-planar surface of the bone to detect forces and strains experienced by the non-planar surface of the bone, due to a blunt force event that originates external to the dermal layer, at a respective location on the bone where each force sensor and the strain gauge are located;

wherein each of the independently bendable fingers extend from a common bending region of the flexible thin-film substrate;

wherein a sensor interface, a center measurement point disposed at the central force sensor, and the common bending region are aligned along a linear relationship;

wherein a finger of the independently bendable fingers extends from the common bending region at a non-perpendicular angle to the linear relationship to conform to a curvature of the non-planar surface of the bone and place the first peripheral force sensor secured at a distal end of the finger in contact with the bone.

19. The method of claim 18, wherein the finger is a first finger of the flexible thin-film substrate;

the first peripheral force sensor is disposed at a distal end of athe first finger of the flexible thin-film substrate, the second peripheral force sensor is disposed at a distal end of a second finger of the flexible thin-film substrate, the strain gauge is disposed at a distal end of a third finger of the flexible thin-film substrate, and the flexible thin-film substrate comprises voids among the first finger, the second finger, and the third finger to permit each of the first finger, the second finger, and the third finger to bend about at a respective finger base relative to each other to conform the blunt force sensor array to the non-planar surface.

20. The method of claim 18, wherein a thickness of the blunt force sensor array at any of the sensing areas is less than about 0.5 millimeters.

* * * * *